United States Patent [19]
McKeel

[11] Patent Number: 5,916,184
[45] Date of Patent: Jun. 29, 1999

[54] ORTHOPEDIC AIRFLOW AND WATER PROOF CAST PADDING MATERIAL AND METHOD OF MAKING A CAST

[76] Inventor: William H. McKeel, P.O. Box 2237, Springfield, Mo. 65801

[21] Appl. No.: 09/015,483

[22] Filed: Jan. 28, 1998

[51] Int. Cl.$^6$ .................................................. A61F 5/04
[52] U.S. Cl. ..................... 602/6; 602/3; 602/5; 428/71
[58] Field of Search ........................... 602/6, 3, 5; 428/71

[56] References Cited

U.S. PATENT DOCUMENTS

| | | | |
|---|---|---|---|
| 2,958,325 | 11/1960 | Claydon et al. | 602/6 |
| 3,307,537 | 3/1967 | Simon et al. | 602/14 |
| 3,882,857 | 5/1975 | Woodall, Jr. | 128/90 |
| 3,998,220 | 12/1976 | Cleer, Jr. et al. | 128/91 |
| 4,387,710 | 6/1983 | Beatty, III | 128/91 |
| 4,573,456 | 3/1986 | Spann | 128/80 |
| 4,766,890 | 8/1988 | Hollrah | 128/89 |
| 4,888,225 | 12/1989 | Sandvig et al. | 428/71 |
| 4,928,678 | 5/1990 | Grim et al. | 128/90 |
| 4,946,726 | 8/1990 | Candvig et al. | 428/76 |
| 5,277,954 | 1/1994 | Carpenter et al. | 428/71 |
| 5,324,252 | 6/1994 | Libby et al. | 602/5 |
| 5,395,305 | 3/1995 | Koide et al. | 602/48 |
| 5,527,265 | 6/1996 | McKeel | 602/6 |

Primary Examiner—Jerome Donnolly
Assistant Examiner—Kelvin Hart
Attorney, Agent, or Firm—Richard J. Grundstrom

[57] ABSTRACT

The orthopedic airflow and waterproof cast padding material of this invention consists of an elongated pad with a top surface, a bottom surface, an inside edge having an overlap region and an outside edge. The pad is made with a water and air impermeable material, such as a thermal foam closed cell polyethylene. The elongated pad can be helically wrapped around a fractured limb to form a cast pad and an immobilizing waterproof cast when wrapped with an air and water permeable waterproof casting tape. The overlap region overlaps a previous wrap as the elongated pad is helically wrapped around a limb or area to be casted. A plurality of cushions project outward from the top surface of the elongated pad between the outside edge and the overlap region. The cushions are placed against the skin as the elongated pad is helically wrapped around a limb. A plurality of air channels between the cushions allow airflow across the top surface of the elongated pad and across the skin of the limb. The air channels also allow water and moisture to run off and out of the cast. A plurality of drain apertures through the elongated pad, located between the cushions and within the air channels, allows water to drain through the elongated pad and allows the cast to breathe.

10 Claims, 5 Drawing Sheets

ORTHOPEDIC AIRFLOW AND WATER PROOF CAST PADDING MATERIAL AND METHOD OF MAKING A CAST

BACKGROUND OF THE INVENTION

The present invention relates to an improved orthopedic airflow and waterproof cast padding material and a method of making a cast and more particularly to a new cast padding material which allows airflow therethrough and which is waterproof and a method of making a waterproof cast which allows drainage of water therefrom and allows airflow therethrough to rapidly dry the skin and interior of the cast.

Typically, most broken limbs, such as arms and legs, are immobilized in a cast for the healing process. The cast immobilizes the limb to allow the bone fracture to mend itself in proper position. The cast most often used consists of layers of fabric and cotton padding tape wrapped around the limb. The layers of fabric and cotton padding tape are covered with plaster or with a newer fiberglass cast. The plaster cast is typically supplied in the form of a casting tape made with a fibrous tape impregnated with plaster. The plaster is wetted to bond the plaster together to form a hard supporting cast. Once bonded the plaster binds together to make a solid plaster cast with a fabric and cotton padding.

The plaster in the casts made in this manner dissolves when wet. Therefore, care must be taken to prevent the cast from getting wet. Additionally, any moisture that gets under the cast wets the fabric and cotton padding tape within the plaster cast. The fabric and cotton padding tape can get wet from washing, bathing, swimming, rain, from perspiration and other such causes. The wet fabric and cotton padding tape causes skin irritation and maceration after a short time. Mildew and bacteria thrive in such an environment and creates an unpleasant odor. Since the plaster cast cannot be wetted, washing and cleaning is very difficult and skin irritants and dirt cannot be washed out.

The plaster cast is also heavy and rigid and it does not allow for swelling and reduction in the limb. The plaster cast most often cannot be made until the swelling in the limb has gone down. If placed before the swelling is reduced, the cast will become too loose and become ineffective in immobilizing the limb. If the cast is place too early and the limb is still swelling, the cast will be come too tight and create pressure. When swelling occurs or continues after the cast has been placed, the cast often has to be split to relieve pressure.

The fiberglass cast which is also in use today has some advantages over the plaster cast, but has several problem of its own, in addition to some of the same problems encountered with the plaster cast. The fiberglass cast itself is lighter, air permeable, water resistant and more durable than the plaster cast. However, the fabric and cotton padding against the skin may become wet just as in the plaster cast. If this happens, the cast has to be removed to eliminate odors, mildew, and skin irritation just as in the plaster cast. There is no means to dry the cloth padding under the cast once it becomes wet. The fiberglass cast is also rigid like the plaster cast. It does not adjust for swelling and reduction to provide a better and more comfortable fit.

An orthopedic airflow cast pad and method is introduced in U.S. Pat. No. 5,527,265, issued to William McKeel, which addresses these problems. This patent provides for a waterproof cast pad when used in conjunction with a water resistant tape forms a waterproof cast. However, it has been found that the pad creates "pockets" at the elbow, ankle and other places where a bend is encountered due to the bend itself and the pad forming a pocket at the bend. The pocket collects water which may be difficult to remove. This is due to the cast pad being a sheet of waterproof padding without drain holes, which is cut to size, wrapped around the affected area and circled taped. This invention overcomes these problems.

There are also various foam and plastic materials used in making casts. Some of these material are water and air permeable. However, in almost all instances the permeability rate for water or moisture transmission is very slow. This results in a water logged cast, which makes it heavy and uncomfortable. In addition, the holding of moisture also promotes bacteria and mildew to form. This invention overcomes this problem.

Accordingly, it is an object of the present invention to provide an orthopedic airflow and waterproof cast padding material and method of making a cast adapted to overcome the disadvantages of the plaster cast, fiberglass cast and some foam casting materials that are typically used today and known in the prior art. With the orthopedic airflow and waterproof cast padding material and method of making a cast of this invention will result in a cast will fit better, help to reduce slippage, adjust to normal swelling and shrinkage of the callus around the fractured bone, reduce likelihood of developing pockets where water may accumulate and has airflow therethrough to aerate the skin and to promote drying and healing.

Another object of the present invention is to provide an improved orthopedic airflow and waterproof cast padding material and method of making a cast constructed to provide a light weight cast pad and cast for immobilizing a fractured limb that is water resistant. Since the orthopedic airflow and waterproof cast padding material and method of making a cast of this invention is water resistant, irritants and other matter can be flushed out without affecting the cast, the cast padding or the fit. This helps to eliminate skin maceration, itching and odors associated with typical fabric and cotton padding used with a plaster or fiberglass casts and allows frequent washing without impacting the effectiveness or integrity of the cast.

A further object of the present invention is to provide an orthopedic airflow and waterproof cast padding material and method of making a cast that promotes airflow between the skin and the cast. The orthopedic airflow and waterproof cast padding material and method of making a cast of this invention contains multiple air channels to allow airflow to the skin. These air channels provides a means of irrigating and washing the skin under the cast and to provide a means of allowing water and moisture to runoff. The materials used are water impermeable and air impermeable which makes a cast which easily sheds water without becoming water logged or which will not hold moisture contrary to some previous known and used materials.

Still another object of the present invention is to provide an orthopedic airflow and waterproof cast padding material and method of making a cast having universal application which is adapted for easy application by a physician and to maintain cost to a minimum for the patient. The orthopedic airflow and waterproof cast padding material and method of making a cast of this invention is easily applied by following simple instructions.

Yet another object of the present invention is to provide an orthopedic airflow and waterproof cast padding material and a method of making a cast having means to drain water from the cast and in particular a means of eliminating water accumulation at bends within the cast. It has been found that the improvement and features of the present invention allow water to drain very effectively and promotes drying in a relatively short period of time.

SUMMARY OF THE INVENTION

To accomplish the foregoing and other objects of this invention there is provided an orthopedic airflow and waterproof cast padding material and method of making a cast and more particularly a cast pad that is light weight, water resistant which is easily applied to immobilize a fractured limb.

The orthopedic airflow and waterproof cast padding material and method of making a cast of this invention has an elongated pad with a top surface, a bottom surface, an inside edge and an outside edge. The pad is made with a water and air impermeable material, such as a thermal foam closed cell polyethylene. The elongated pad can be wrapped around a fractured limb to form a cast pad and an immobilizing waterproof cast when wrapped with an air and water permeable waterproof casting tape. The elongated pad typically will have an overlap region along one edge. The overlap region overlaps a previous wrap as the elongated pad is wrapped around a limb or area to be casted. A plurality of cushions project outward from the top surface of the elongated pad between the outside edge and the overlap region. The cushions are placed against the skin as the elongated pad is wrapped around a limb. A plurality of air channels are formed between the cushions to allow airflow across the top surface of the elongated pad and across the skin of the limb. The air channels also allow water and moisture to run off and out of the cast. A plurality of drain apertures through the elongated pad are located between the cushions and within the air channels. The drain apertures allows water to drain through the elongated pad and allows the cast to breathe.

The elongated padding can be made in various sizes based on the particular application. The cushions can and may also vary in size and firmness to accommodate the needs of the patient, from infants to large adults. In addition, the elongated pad can easily wrap around any limb or any portion thereof.

The elongated pad with cushions allows water and air flow to the skin to reduce rashes, skin maceration and itching under the cast and to allow flushing or washing the area under the cast. The material used is water impervious to allow rinsing under the cast, eliminate odor and collection of water, and reduce moisture against the skin. The elongated pad and cushions also adjusts to swelling and reduction in swelling for a more consistent fit of the cast.

These and other objects and features of the present invention will be better understood and appreciated from the following detailed description of the main embodiment thereof, selected for purposes of illustration and shown in the accompanying drawings.

DETAILED DESCRIPTION

Figure 1:
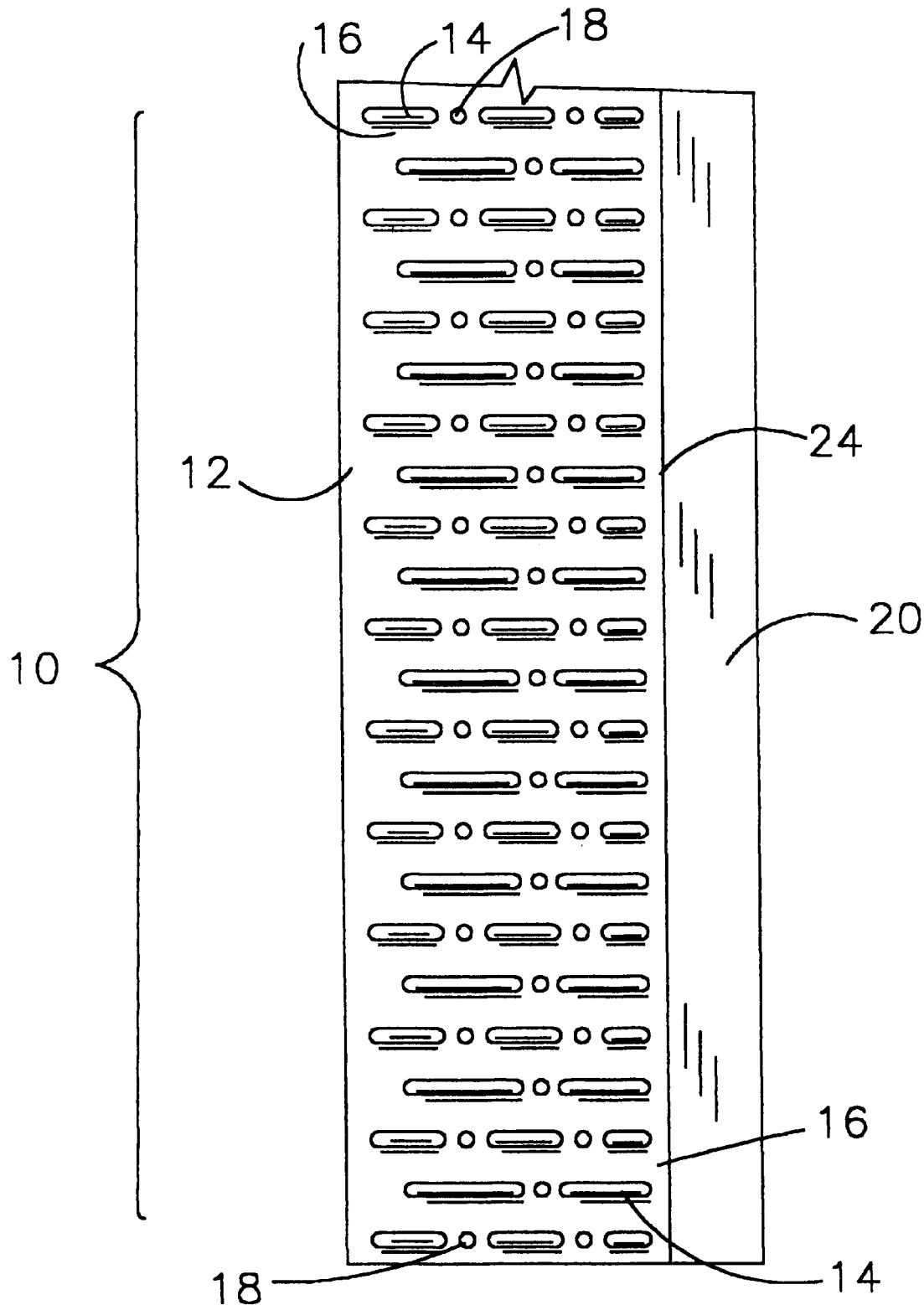
FIG. 1 is a view of the top surface showing the arrangement of the cushions, air channels and drain apertures of the orthopedic airflow and waterproof cast padding material and method of making a cast of this invention.
Figure 2:
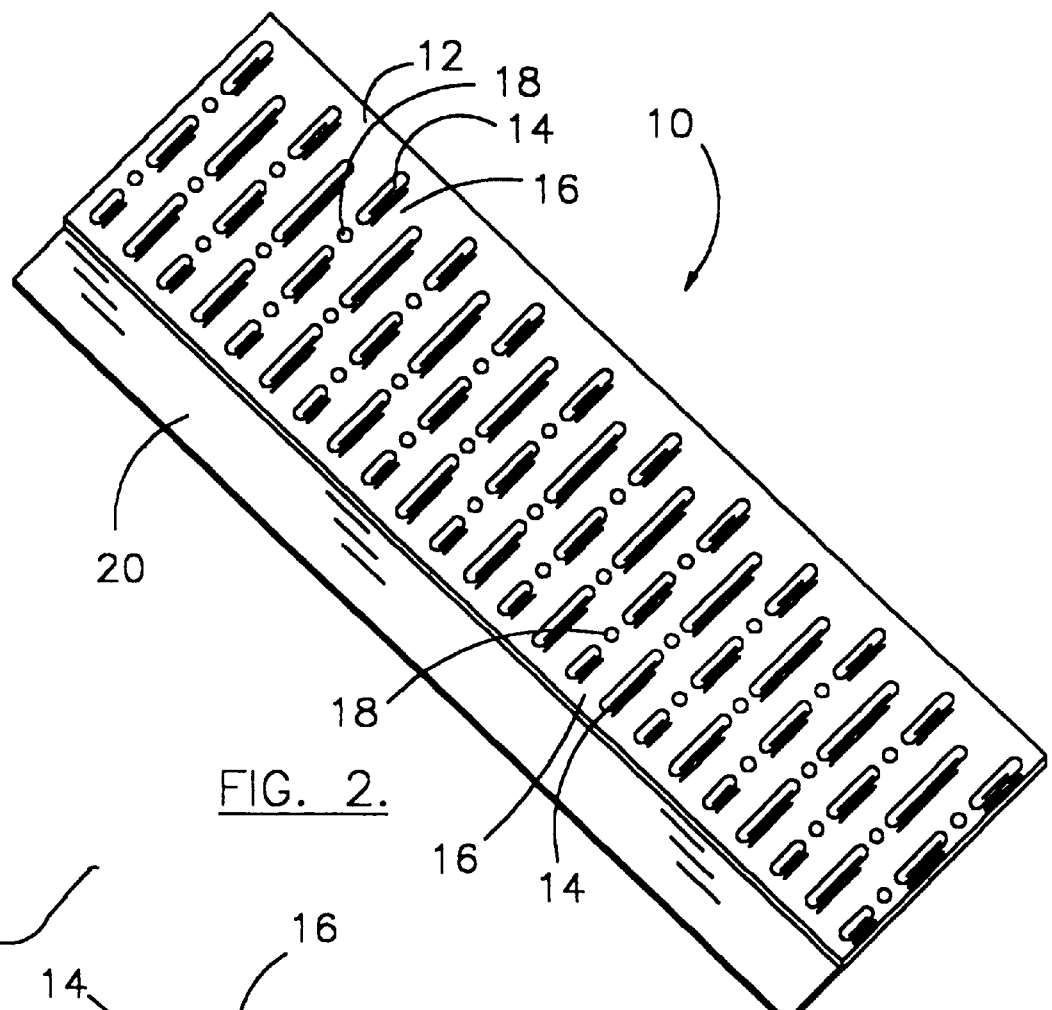
FIG. 2 is an isometric view showing the top surface of the preferred embodiment of the orthopedic airflow and waterproof cast padding material and method of making a cast.
Figure 3:
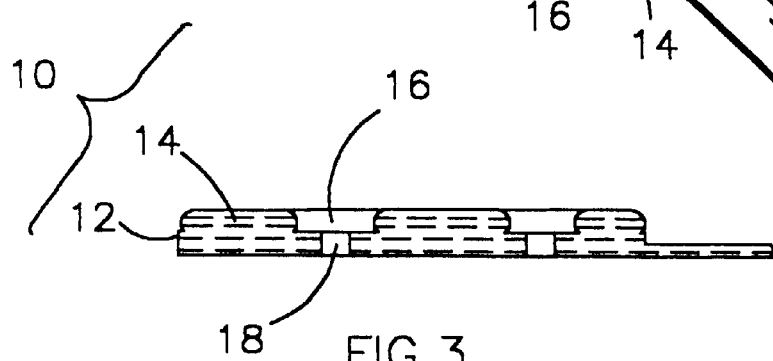
FIG. 3 is an crosswise sectional view of the orthopedic airflow and waterproof cast padding material and method of making a cast.
Figure 4:
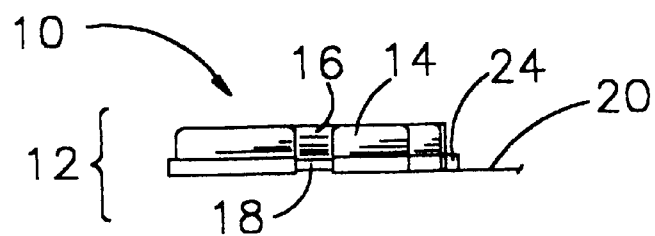
FIG. 4 is an end view of the orthopedic airflow and waterproof cast padding material and method of making a cast.
Figure 5:
FIG. 5 is a side view of the orthopedic airflow and waterproof cast padding material and method of making a cast.
Figure 6:
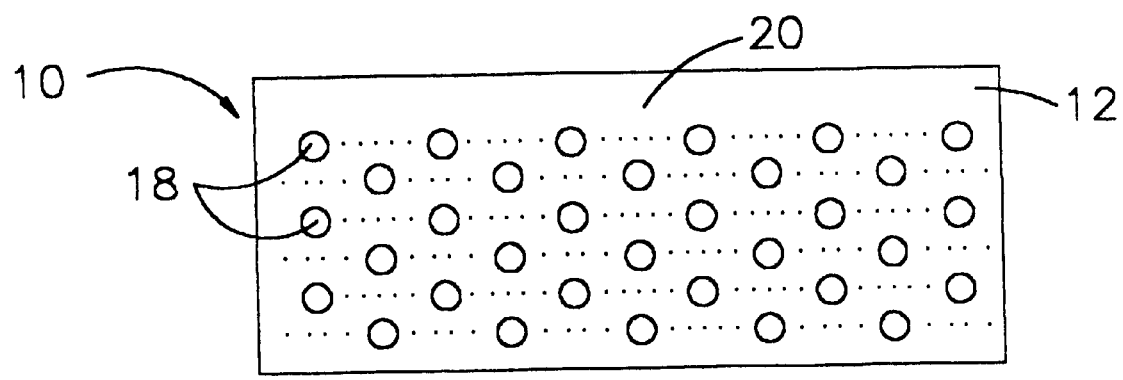
FIG. 6 is a bottom view of the orthopedic airflow and waterproof cast padding material and method of making a cast.
Figure 7:
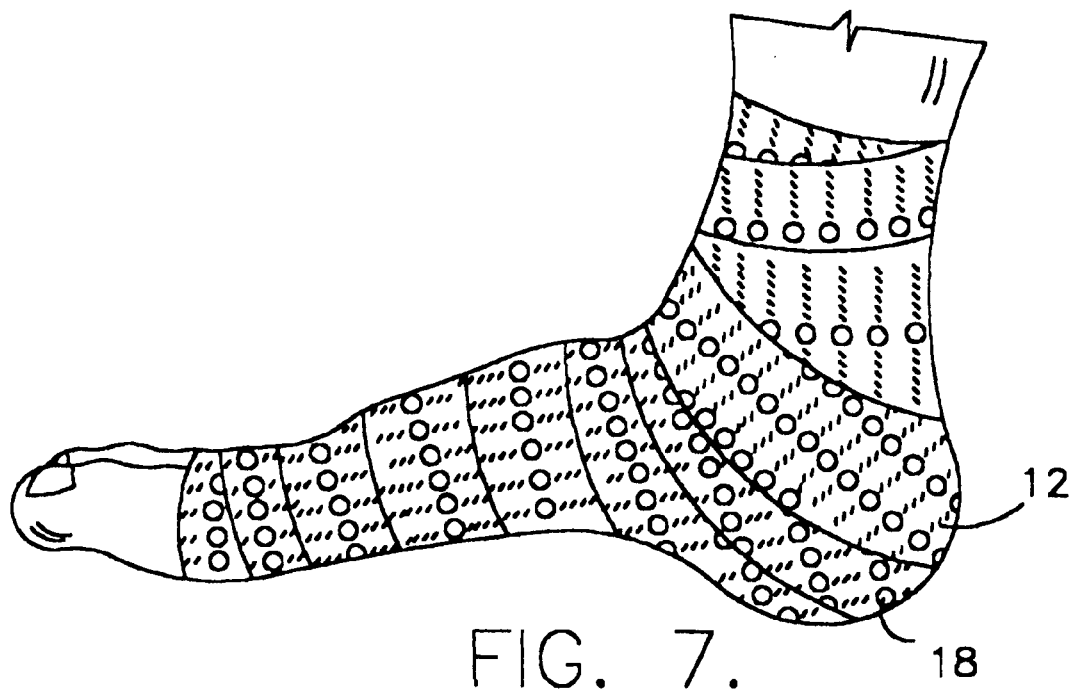
FIG. 7 shows the elongated pad being wrapped around a limb, specifically a foot and ankle, to be casted.
Figure 8:
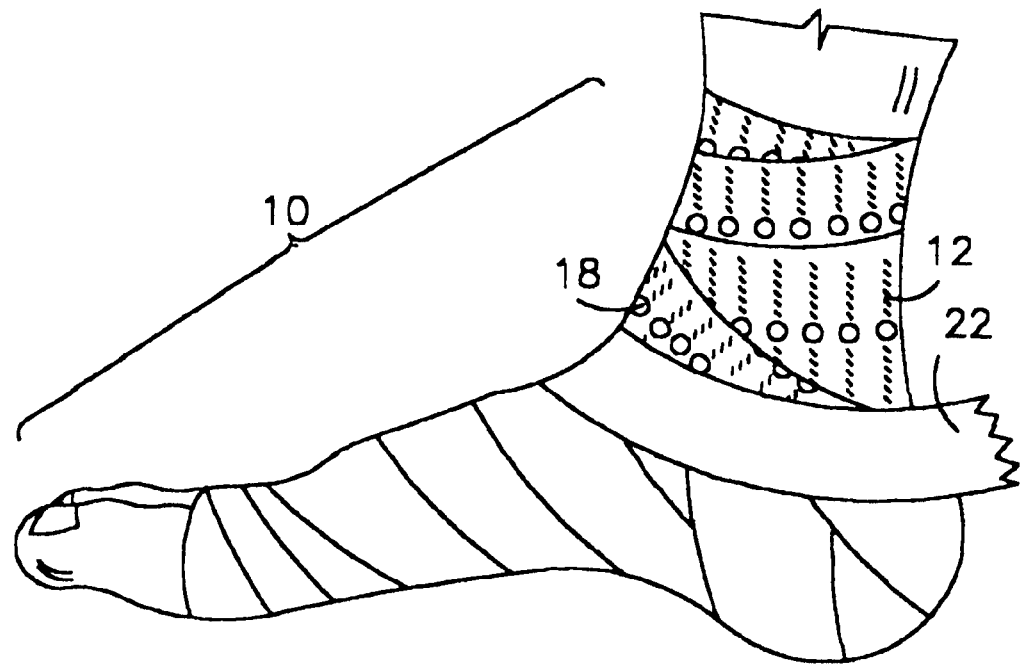
FIG. 8 shows the orthopedic airflow and waterproof cast padding material and method of making a cast wrapped on an ankle and being wrapped with a water and air permeable casting tape to form a cast which immobilizes the limb.
Figure 9:
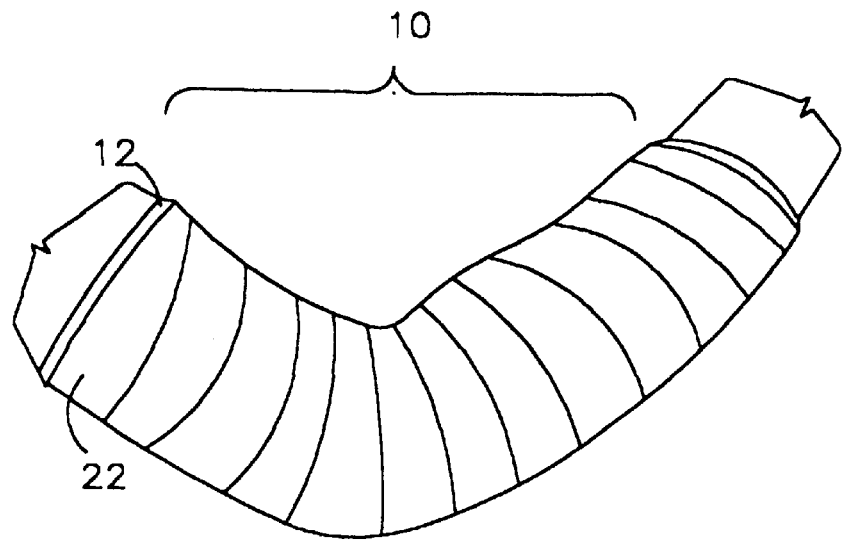
FIG. 9 shows a cast made with the orthopedic airflow and waterproof cast padding material and method of making a cast of this invention on an elbow.
Figure 10:
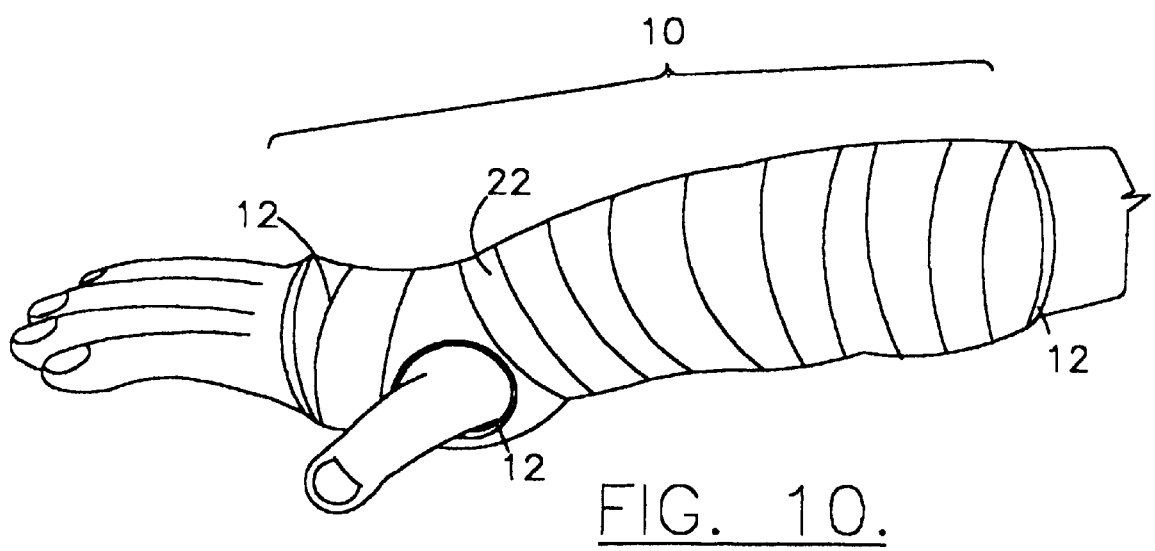
FIG. 10 shows a cast made with the orthopedic airflow and waterproof cast padding material and method of making a cast of this invention on a wrist.

Referring now to the drawings, FIGS. 1–5, there is shown the preferred embodiment of the orthopedic airflow and waterproof cast padding material 10 of this invention. FIGS. 6–8 shows a cast being made with the orthopedic air flow and waterproof cast padding material 10 of this invention. FIGS. 9 and 10 show a cast made with the orthopedic airflow and waterproof cast padding material of this invention on two additional applications.

The orthopedic airflow and waterproof cast padding material and method of making a cast 10 of this invention consists basically of an elongated pad 12, a plurality of cushions 14, a plurality of air channels 16 formed between the cushions 14, a plurality of drain apertures 18 between cushions and within the air channels 16 and an overlap region 20.

The elongated pad 12 as presented herein is easily wrapped around a limb, at any location, including: elbows, wrists, knees and feet. It the past, similar inventions could not be easily formed around corners or bends in the limbs. Since the elongated pad 12 is provided in a long strip, it can be easily wrapped around the area. This prevents cupping or the formation of a pocket and the accumulation of liquids therein. The elongated pad 12 is universally applied to practically any fracture that a plaster or fiberglass cast may be used. The airflow and waterproof cast padding of this invention is intended to replace the fabric and cotton padding used with plaster and fiberglass immobilizing casts.

The preferred embodiment and the best mode contemplated of the orthopedic airflow and waterproof cast padding material and method of making a cast 10 of the present invention are herein described. However, it should be understood that the best mode for carrying out the invention hereinafter described is offered by way of illustration and not by the way of limitation. It is intended that the scope of the invention include all modifications that incorporate its principal design features.

The elongated pad 12 and cushions 14, in the preferred embodiment, are formed from a single elongated strip of a water impermeable and air impermeable material. The elongated pad 12 and cushions 14, in the best mode contemplated, are molded from a single sheet of water and air impermeable closed cell thermal foam polyethylene. This material, closed cell thermal foam polyethylene, has been found to provide adequate compression and expansion to allow for swelling and reduction of the limb for a better fit and to reduce slippage. It is also water impermeable to allow washing and flushing of irritants. Since the material is impermeable to air and water, the material sheds water very easily and quickly. This eliminates absorption of moisture into the cast, which can cause skin maceration, mildew or bacteria buildup, order and discomfort.

The air channels 16 allows air flow between the elongated pad 12 and patient's skin as well as allowing water and moisture to runoff. The ability to wash and flush under the cast and cast padding minimizes rashes and itching and helps to eliminate odors.

When used with fiberglass or plastic cast wrap there is less weight and more comfort than the conventional plaster cast. Since these wraps are also water resistant, the patient can wash, bath and take showers without much regard to the cast. The cast can be dripped dried by placing the cast at a slight angle or air can be blown into the air channels 16. The pattern of the air channels 16 will provide airflow to the majority of the skin surface under the cast. The airflow will pickup and remove moisture from under the cast padding and from within the cast. These are vast improvements over the conventional plaster cast using fabric and cotton padding and it is also the first major change in providing an orthopedic cast padding and a method of making a waterproof cast.

The exact process of manufacture may vary, however, it is expected to be produced in the most cost effective method. Typically, the elongated strip 12 will be made by a molding process. The strip or elongated pad 12 will be fed through a radiant heated tunnel oven and go through a roll or flat mold to form the cushions 14, the air channels 16 and the overlap region 20. The drain apertures 18 are formed by feeding the elongated pad 12 through a die cutter. The elongated pad 12 is then rolled and packaged.

The elongated pad 12 of the orthopedic airflow and waterproof cast padding material and method of making a cast 10, in the best mode contemplated, is available in different sizes and with different compression characteristics depending on the application. The elongated pad 12 will typically come in rolls. Each roll will typically be a strip of either six feet or eight feet in length or vary to meet casting needs. Excess lengths can always be cut off with a pair of scissors when applied. Widths can also vary, but in the preferred embodiments and best mode contemplated, the widths will be two and one quarter inches, three and one quarter or four and one quarter inches wide. These widths will typically fit most applications. Other widths and lengths may be made as desired or as the market forces dictate.

A plurality of cushions 14 project outward from the top surface of the elongated pad in a specific pattern, in the preferred embodiment. The cushions 14, in the best mode contemplated are formed by molding as described above. The cushions 14 can be made in varying size and firmness to accommodate infants to large adults. In the preferred embodiment and best mode contemplated, the pattern of cushions 14 are arranged in a series of cushions in a plurality of parallel rows. Each cushion 14, in the best mode contemplated, will be one inch to one and a quarter (1 ¼) inches long, one quarter (¼) inch wide and projecting outward from the elongated pad 12 one quarter (¼) inch.

The cushions 14 in each row are separated by spaces. Each space between the cushions 14 are one quarter (¼) of an inch. The cushions 14 and spaces between the cushions are staggered in alternating rows. This pattern staggers the spaces from row to row.

The pattern of cushions 14 creates a plurality of air channels 16. The air channels 16 in this pattern allows airflow both length wise and cross wise across the top surface 18 of the elongated pad 12. Cross wise the air channels 16 are straight between and parallel with the rows. Length wise the air channels 16 are staggered through the staggered spaces between cushions 14 in the rows. The spaces are staggered to maximize air flow to the skin. The staggered spaces will prevent air from just flowing straight through and will better support the injured limb.

A plurality of air apertures 18 are provided to drain water or other liquids from the inside of the cast. The drain apertures 18 are made as indicated above, in the preferred embodiment. Typically, the air apertures 18 will have a quarter (¼) inch diameter and will be located between the cushions 14 and within the air channels 16. However, other sizes would also satisfy the needs and are intended to be within the scope of this disclosure.

The drain apertures 18 prevent accumulation of liquids in locations such as the elbow, wrist, knee, ankle, foot or any other location. In the past, liquids could accumulate in such areas. This would allow the possibility of skin maceration, mildew, odor, bacterial growth and discomfort. This problem is eliminated by the drain apertures 18. The drain apertures 18 also allows air to enter and exit along the entire cast. This creates a "breathing effect" for the cast. This also helps to promote drying when wet, elimination of order, and to promote healthy skin.

An overlap area 20 is also provided. In the preferred embodiment and in the application of the elongated pad 12, the overlap region 20 will overlap the previous wrap as the elongated pad 12 is wrapped around the limb being casted. The overlap region 20 will typically be made by roll pressing to a thickness of approximately one sixteenth (¹⁄₁₆) of an inch and having a width of one inch. The exact dimensions can vary depending on the model, style and application. The width and thickness can vary as demanded.

The overlap region 20 is provided to prevent gaps from appearing as the elongated pad 12 is wrapped around a limb. If gaps were present, the casting tape could contact the skin and cause discomfort and skin irritation. The overlap region 20 ensures that the hard supporting casting material of the casting tape 22 will not come into contact with the skin or tissue of the patient, particularly in areas of bends or abrupt body size changes, such as at the ankle, the heel and foot, the elbow, and the wrist and hand. The overlap region 20 also provides the doctor a guide line for uniform application when wrapping the elongated pad 12 around a limb.

The orthopedic airflow and water proof cast padding material and method of making a cast 10 of this invention can also be incorporated with an anti-fungal and/or anti-bacteria ingredients now known or later developed. These anti-fungal and anti-bacterial ingredients can be directly incorporated within the material which the elongated pad 12 is made or can be incorporated by a separate attachment or element 24 added hereto. As illustrated by way of demonstration, an anti-bacterial or anti fungal element can be incorporated along the overlap region 20. The exact manner of incorporation would of course depend on the type of anti-bacterial or anti-fungal material being utilized. Any method or manner of incorporating the anti bacterial or anti fungal material which is compatible with elongated pad 12 disclosed herein is considered within the scope and limitations of this invention.

In use, the orthopedic airflow and waterproof cast padding material and method of making a cast 10 is used to immobilize a fractured limb such as an arm or leg or any portion thereof. It is intended to be used in place of the traditional fabric and cotton padding that is now used with the plaster cast or newer fiberglass cast. Referring now to FIGS. 7 and 8, an ankle is used to illustrate how the orthopedic airflow and waterproof cast padding material and method of making a cast 10 is used. FIGS. 9 and 10 show other problem areas casted with this invention, including the wrist and elbow. These figures show that they are easily casted using the methods herein disclosed.

The ankle or area to be casted, is completely wrapped with the elongated pad 12. It will be wrapped in a helical or spiral manner around the limb. The cushions 14 are positioned against the skin. The elongated pad 12 is wrapped such that overlap region 20 overlaps the preceding wrap. Once the area to be casted is completely wrapped any excess material is cut off or trimmed. A common scissors can be used for this task.

In some instances, the bottom surface could also be placed against the skin. This would provide a water resistant cast with additional support. This arrangement would still provide all the benefits discussed herein except reduced airflow to the skin. Since the bottom surface is mainly flat the airflow would be more restricted.

It is also possible, in another embodiment not shown, to have cushions 14 projecting outward from the bottom surface as well as the top surface 18. This embodiment results in a reversible orthopedic airflow and waterproof cast padding material and method of making a cast 10 that can be used with equal results either way.

After the area to be casted is completely wrapped with the elongated pad 12, it is wrapped with an air permeable fiberglass casting tape, plastic casting wrap or other water-resistant casting tape 22 to form a complete water resistant immobilizing cast. Approximately one half (½) inch at both ends of the wrapped elongated pad 12 are left exposed to prevent the air channels 16 from being blocked and to provide padding between the end of the hard cast and the patient's skin. The casting tape 22 used should be air and water permeable. Air and water permeability allows water to drain, and air to enter and exit along the entire cast. It also allows the cast to breathe.

In extreme situations, the completed cast may be covered with as a plaster covering, as a with typical cast, to provide a more rigid cast. This would only be necessary in extreme cases where the additional rigidness is needed. It is not anticipated that plaster would be used or needed very often. When plaster is used, the plaster could become wet. As such, some advantages of the cast made in accordance with this invention are obviously lost.

The orthopedic air flow and waterproof cast padding material and method of making a cast 10 of this invention over comes all the disadvantages previously mentioned above plus many more. The cast using the airflow and waterproof cast padding material made in accordance with this disclosure contains many advantages. This includes: elimination of skin maceration, unpleasant odors, water retention, mildew and/or bacterial growth. It provides a cast which the patient can bath, shower, go swimming or go out in the rain without having to worry about getting the cast padding and cast wet. The cast will not have to be wrapped in plastic to protect the plaster and to prevent the padding from getting wet as typically done. It eliminates all bathing difficulties and even allows swimming, with the doctors permission of course.

Warm water and/or soapy water can be flushed through the cast to wash the skin and the inside of the cast. Since all materials are waterproof there is no harm nor a need to replace the cast and cast padding because of wetness. The water is simply drained from the cast by tilting to eliminate the majority of the water. Water will also exit through the drain apertures 18 and through the water permeable casting tape 22. Air flow through the air channels 14 promote further drying by picking up the moisture and carrying it out. Attachments to direct and force air through the cast may also be used to enhance rapid drying if desired. Since the casting tape 22 is air permeable and used in conjunction with the air channels 14 and drain aperture 20 the skin will have adequate air to properly breathe and to eliminate moisture.

Having described the invention in detail, those skilled in the art will appreciate that modifications may be made of the invention without departing from the spirit of the inventive concept herein described.

Therefore, it is not intended that the scope of the invention be limited to the specific and preferred embodiments illustrated and described. Rather, it is intended that the scope of the invention be determined by the appended claims and their equivalents.

What is claimed is:

1. An orthopedic airflow and waterproof cast padding material comprising:

an elongated pad having a top surface, a bottom surface, an inside edge and an outside edge, said pad being made from a strip of water and air impermeable material, said elongated pad being helically wrapable around a fractured limb to form a cast pad and an immobilizing waterproof cast when wrapped with an air and water permeable waterproof casting tape;

an overlap region along said inside edge of said elongated pad, said overlap region overlapping a previous wrap as said elongated pad is wrapped around a limb or area to be casted;

a plurality of cushions projecting outward from said top surface of said elongated pad between said outside edge and said overlap region, said cushions being placed against the skin as said elongated pad is wrapped around a limb;

a plurality of air channels formed between said cushions to allow airflow across said top surface of said elongated pad and across the skin of the limb; and a plurality of drain apertures through said elongated pad located between said cushions and within said air channels, said drain apertures allowing water to drain through said elongated pad.

2. The orthopedic airflow and waterproof cast padding material as set forth in claim 1 in which said cushions comprise a plurality of parallel rows of uniform inline cushions, each row having a plurality of cushions, each cushion separate from another by a space, and said space between said cushions in said rows being staggered from row to row, said cushions making said air channels straight between and parallel with said rows and staggered lengthwise in regards to the elongated pad.

3. The orthopedic airflow and waterproof cast padding material as set forth in claim 1 in which said elongated pad and said cushions are formed from a single elongated strip of air and water impermeable closed cell thermal foam polyethylene.

4. The orthopedic airflow and waterproof cast padding material as set forth in claim 3 in which said elongated pad and said cushions are molded from thermal foam closed cell polyethylene.

5. The orthopedic airflow and waterproof cast padding material as set forth in claim 1 further comprising an antifungal and/or antibacterial ingredients incorporated within the material of said elongated pad.

6. The orthopedic airflow and waterproof cast padding material as set forth in claim 1 further comprising an antifungal and/or an antibacterial element contained within said elongated pad.

7. An orthopedic airflow and waterproof cast padding material comprising:

a elongated pad formed from an elongated strip of an air and water impermeable material having a top surface and a bottom surface;

an overlap region along one side of said elongated pad;

a plurality of cushions projecting outward from said top surface of said elongated pad;

a plurality of air channels formed between said cushions to allow airflow across skin of a casted limb and across said top surface of said elongated pad; and a plurality of drain apertures through said elongated pad, said drain apertures being between said cushions and within said air channels.

8. The orthopedic airflow and waterproof cast padding material as set forth in claim 7 in which said elongated pad further contains an inside edge and an outside edge, said pad being made with a water and air impermeable material, said elongated pad being helically wrapable around a fractured limb to form a cast pad and an immobilizing waterproof cast when wrapped with an air and water permeable waterproof casting tape.

9. The orthopedic airflow and waterproof cast padding material as set forth in claim 7 in which said cushions comprise a plurality of parallel rows of uniform inline cushions, each row having a plurality of cushions, each cushion separate from another by a space, and said space between said cushions in said rows being staggered from row to row, said cushions making said air channels straight between and parallel with said rows and staggered lengthwise in regards to the elongated pad.

10. The orthopedic airflow and waterproof cast padding material as set forth in claim 7 in which said elongated pad and cushions are molded from a closed cell cross linked polyethylene.

* * * * *